United States Patent [19]
Cotter

[11] Patent Number: 5,762,646
[45] Date of Patent: Jun. 9, 1998

[54] BLOOD COLLECTION SYSTEM AND COUPLING

[75] Inventor: Robert F. Cotter, Duxbury, Mass.

[73] Assignee: Duxbury Scientific, Inc., Duxbury, Mass.

[21] Appl. No.: 722,975

[22] Filed: Sep. 30, 1996

[51] Int. Cl.$^6$ .................. A61M 1/00; F16L 15/00
[52] U.S. Cl. .................. 604/410; 604/905; 604/283; 285/303
[58] Field of Search .................. 604/403, 410, 604/411, 414, 415, 905; 285/303, 360, 361, 376, 396, 401, 402

[56] References Cited

U.S. PATENT DOCUMENTS

| | | | |
|---|---|---|---|
| 219,098 | 9/1879 | Jewell | 285/303 |
| 2,580,725 | 1/1952 | Breckenridge | 285/361 |
| 2,795,438 | 6/1957 | Oetiker | 285/376 |
| 2,885,223 | 5/1959 | Duff | 285/303 |
| 3,858,910 | 1/1975 | Oetiker | 285/376 |
| 4,076,285 | 2/1978 | Martinez | 604/905 |
| 4,396,382 | 8/1983 | Goldhaber | 604/410 |
| 5,211,642 | 5/1993 | Clendenning | 604/410 |
| 5,344,414 | 9/1994 | Lopez et al. | 604/905 |
| 5,492,147 | 2/1996 | Challender et al. | 604/905 |

*Primary Examiner*—John G. Weiss
*Assistant Examiner*—David J. Cho
*Attorney, Agent, or Firm*—George W. Neuner

[57] ABSTRACT

A coupling and system for collecting blood or other biological fluids are described. The system includes first and second containers and a coupling for joining the containers. The coupling holds the containers together in two different longitudinal positions both positions preventing contamination. In a first position, the containers are held so that there is no flow between the containers. In a second position, the containers are held so that flow of blood is permitted between the containers.

11 Claims, 5 Drawing Sheets

BLOOD COLLECTION SYSTEM AND COUPLING

FIELD OF THE INVENTION

This invention is directed to a new and improved biological fluid collection system and, particularly, to a new coupling device that provides a contamination free pathway between two containers, while providing the ability to connect the containers with the coupling with the pathway either open or closed, and to disconnect the coupling while fluid sample such as blood remains in the collection container without forming contaminating blood droplets outside of the blood pathway.

BACKGROUND OF THE INVENTION

Biological fluids are collected for a variety of reasons. The collection of a patients own blood has become widely used during surgical procedures and quite often after surgical procedures.

The collected patients blood is reinfused into the patient rather than using blood from donees which may be diseased.

Examples of prior products for collecting blood are shown and described in U.S. Pat. Nos. 4,8350,964; 5,002,529 and 5,052,725, as well as in the patents cited therein.

In copending U.S. Pat. application Ser. No. 08/389,928 filed Feb. 16, 1995, a blood collection system is described wherein a second container or blood bag is coupled to a first container or blood collection chamber in a first position such that the pathway between containers is sealed from contamination prior to transfer of blood from first container to the second container and, then, the coupling member is moved into a second sealing position to permit the transfer of blood from one container to the other. The coupling member should not be separated until the transfer of blood from the collection chamber to the blood bag is completed. If the coupling member is separated prematurely, i.e. while blood remains in the collection chamber, some droplets of blood may fall from the coupling, particularly from the female portion of the coupling.

Thus, it can be seen that new and improved blood collection systems are desired that would prevent blood droplets from forming outside the blood pathway and falling, even though the blood collection system may be disconnected prematurely.

SUMMARY OF THE INVENTION

The present invention providers an improved coupling device that is particularly useful in blood collection systems. Use of the coupling device in a blood collection system permits blood to be easily collected in a first container and then transferred as required to a second container which can be used to reinfuse the blood into a patient.

In accord with the present invention, a coupling device provides a contamination free pathway between opposite ends thereof and can be used to join two containers together in a first position where the pathway connecting the containers is closed and in a second position where the pathway connecting the containers is open.

The coupling comprises a male coupling member and a female coupling member. The male coupling member has a passageway containing a valve assembly with a valve in a normally closed position and a male member having a passageway containing a valve assembly with a valve in a normally closed position. The male member has a first positioning groove that cooperates with the female member to join the male member and the female member together in a first position wherein both valves remain closed to seal the passageway. The male member also has a second positioning groove that cooperates with the female member to join the male member and the female member together in a second position wherein the opposing ends of the coupling are closer together and both valves are open and the passageway is open between opposing ends of the coupling. The positioning grooves are located on the exterior surface of the male member, each groove in a plane perpendicular to the longitudinal axis of the male member, and having a longitudinal groove connecting the two positioning grooves.

The female coupling member is adapted to receive the male coupling member and has a passageway containing a valve assembly with a valve in a normally closed position. A cam is located in the passageway of the female member to cooperate with the grooves on the male member to join the members together. Together, the female coupling member and the male coupling member provide a contamination free pathway between opposing ends of the coupling formed thereby.

This invention permits the second container to be coupled to the first container in a first position such that the pathway between containers is sealed from contamination prior to transfer of blood from one container to another and then moved into a second sealing position in the same coupling member to permit transfer of blood from one container to another. This invention, because of the construction of the coupling, permits the quick automatic closure of the opening to both containers when they are separated from one another by separating the male and female coupling members.

Because of the construction of this system, it readily lends itself to use by hospital staff and makes handling of blood even if contaminated, less dangerous than usual. The construction herein of the system also permits a less costly alternative system to be used in place of current technology.

In this system, there is employed a new and improved coupling system and cooperating valving which permits the aforementioned to be accomplished.

DETAILED DESCRIPTION OF THE INVENTION

Figure 1:
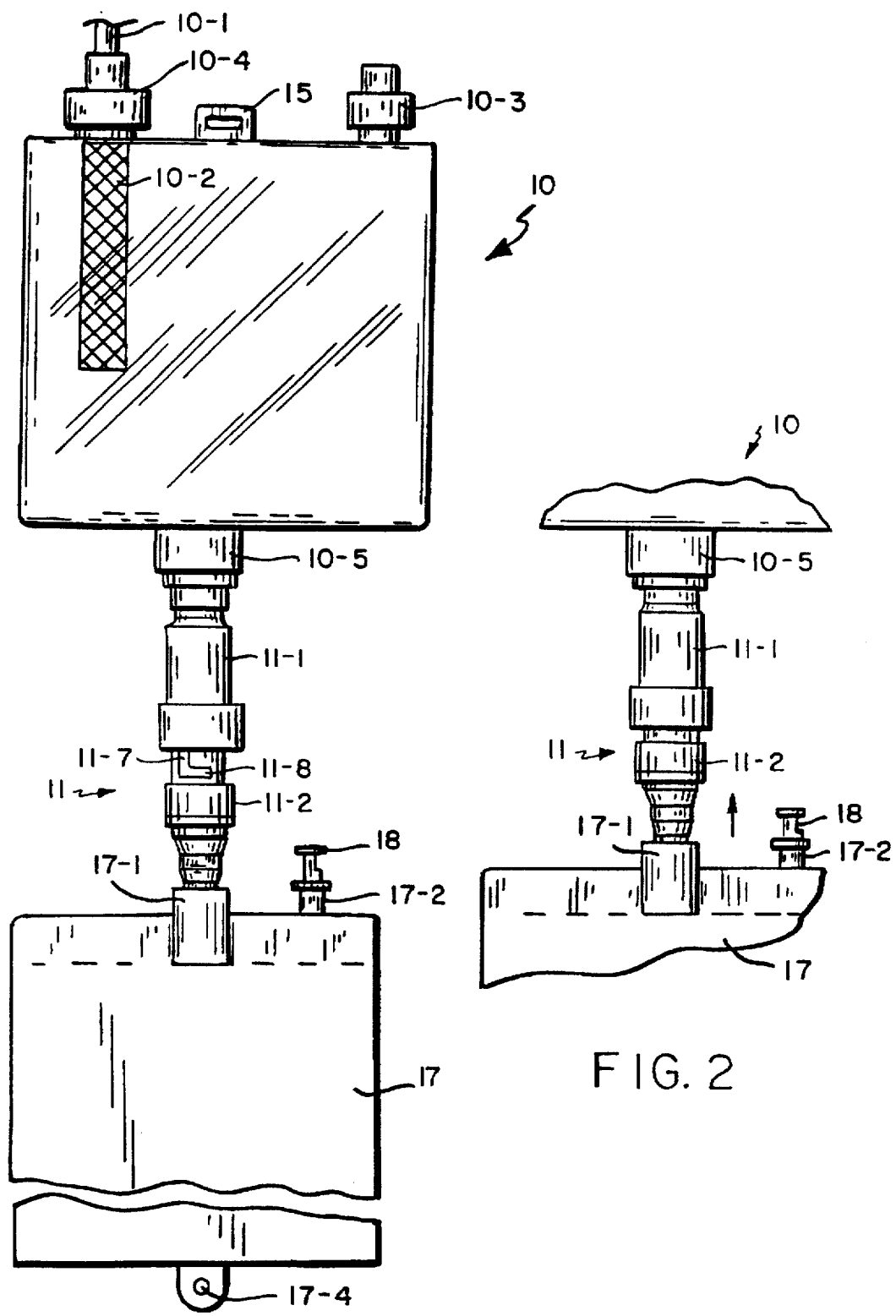
FIG. 1 is a front view of one embodiment of a blood collection system of this invention.
Figure 2:
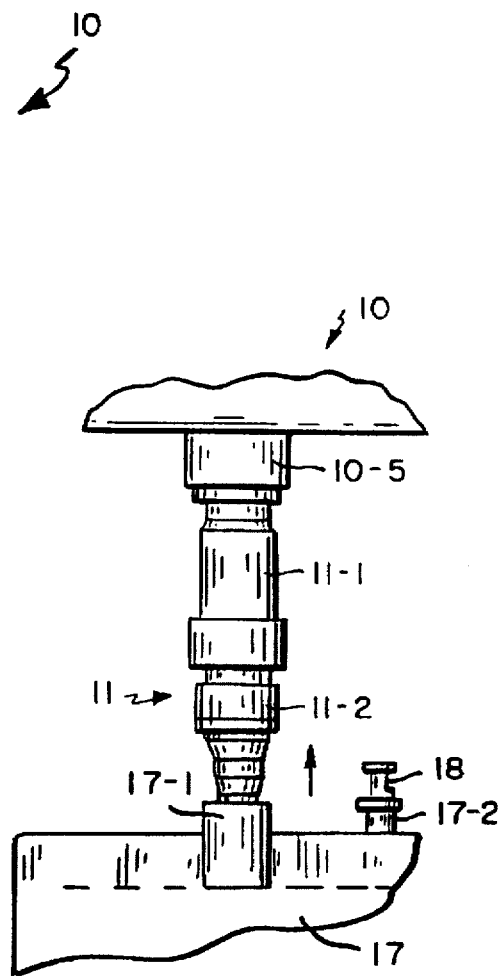
FIG. 2 is a partial view of the blood collection system of FIG. 1 in which the bags are moved relatively closer to one another in comparison to FIG. 1 in order to permit blood to flow from one container into the other.

The invention will be described with reference to the drawings in which certain preferred embodiments are illustrated. With reference to FIGS. 1 and 2, one embodiment of the invention is shown having a fluid collection container 10 connected to a fluid transfer bag 17 with a coupling device 11.

FIG. 1 shows a container 10, preferably a rigid plastic container 10, e.g., for collecting blood. The blood is collected through tubing 10-1 positioned in a coupling projection 10-4 attached to the container and defining an opening. The blood is then passed through a conventional mesh filter 10-2. In some cases suction is applied through tubing and coupling 10-3 to cause the blood to flow into the container 10. Another port may be provided, if desired, in the container 10 to inject anticoagulant. At 10-5 is an opening extending from the bottom of the container 10 into which there is positioned and adhesively joined thereto one female coupling member 11-1 of a two piece preferably plastic coupling device 11. Within the female coupling member 11-1, there is provided a valve assembly and a cam 12 which is located within passageway 20, as will be described later with reference to FIGS. 3 to 5. The valve assembly prevents the flow of blood out of the container 10, except under certain circumstances. The cam 12 cooperates with grooves in the male coupling member to prevent relative longitudinal movement in each of two positions.

The container 10 is usually held in a vertical upright position by use of a strap (not shown) placed through the opening in the projection 15 so that gravity flow of blood from one container to another may take place. At 17, there is shown a second container (bag) preferably of flexible plastic which has openings 17-1 and 17-2 at the top thereof.

In the opening 17-1, there is provided a male coupling member 11-2 joined thereto by adhesive. The male coupling member as shown includes longitudinal positioning grooves, which are shown at 11-8,11-9 (e.g., FIG. 3). A second longitudinal positioning groove (stop) on the connector is not seen in FIG. 1 because the male coupling member is joined with the female coupling member in a first position in a first groove (stop), i.e., in a sealed position wherein longitudinal movement between the two coupling members is prevented.

The bag 17 has the second tube 17-2 adhesively joined thereto for permitting blood in the bag 17 to be withdrawn and reinfused by gravity flow by hanging up the bag by a hook positioned in member 17-4 at the bottom thereof. A removable cap 18 is provided to seal the tube 17-2.

FIG. 2 illustrates the bag 17 moved to a second longitudinal position (i.e., where cam 12 is positioned in groove 11-8) by relatively moving the two containers 10 and 17 closer together. In this position, the cam 12 enters the groove 11-8 to join the bags in the second longitudinal position relative to one another. In this position, as will be described, the valves are then opened to each of the containers so that fluid can be transferred therebetween.

To separate the containers from one another, the male and female coupling members are rotated so that the cam 12 is positioned in a longitudinal groove (i.e., at 11-7 in FIG. 9) in the male coupling member. The coupling members are pulled apart until the cam reaches the end of the groove and the two coupling members can be separated by tipping one member with respect to the other to remove the cam from the groove.

Figure 3:
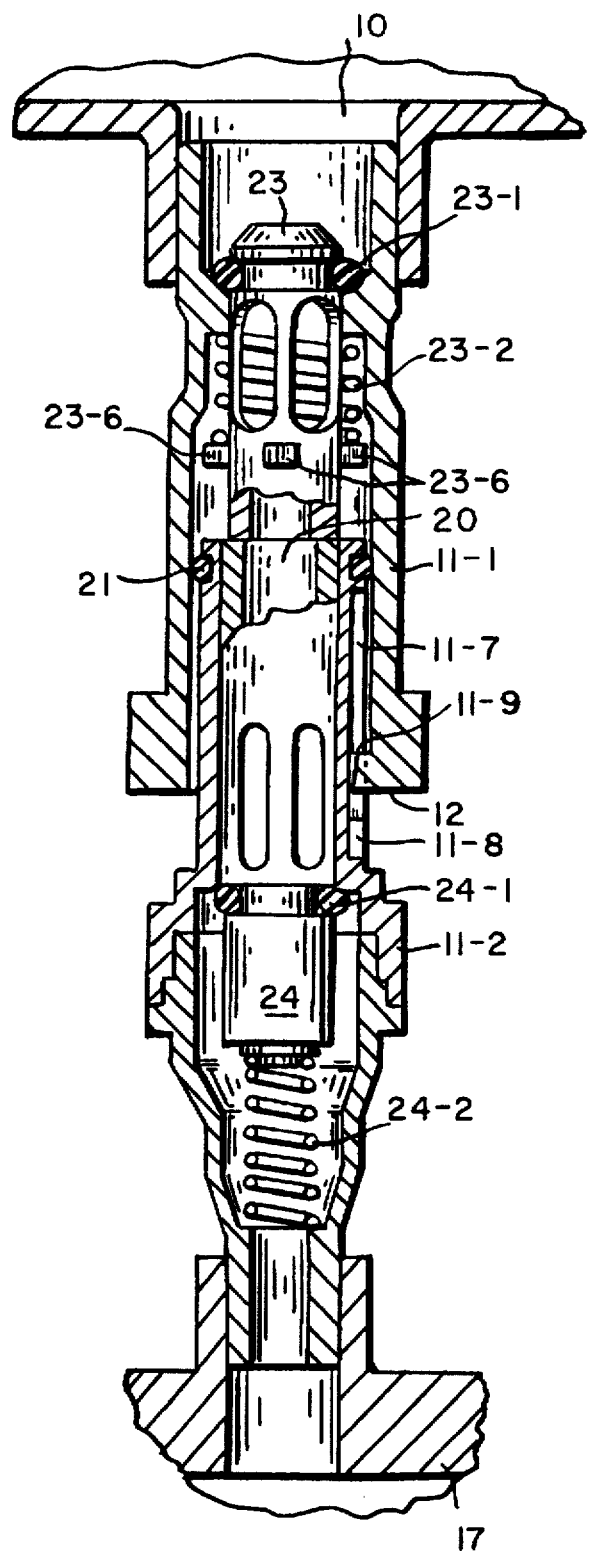
FIG. 3 is a sectional view of the valves and coupling positioned as shown in FIG. 1.

With reference to FIG. 3, valves associated with the coupling device 11 are illustrated. FIG. 3 shows the coupling device 11 when the containers 17 and 10 joined in a first longitudinal position relative to one another and coupled together with the hollow passageway 20 between containers sealed by the coupling and the O-ring 21 supported by the male coupling member 11-2. The prevention of longitudinal movement between the male and female coupling members is the result of cam 12 supported by the female coupling member 11-1 being positioned in groove 11-9 of the male coupling member 11-2.

The female coupling member supports a valve 23 having a spring 23-2 and a sealing O-ring 23-1. The male coupling member supports a second valve 24, which has a spring 24-2 and a sealing O-ring 24-1. The valves 23 and 24 are closed when the coupling members are joined together as shown in FIG. 3. As shown, the valve 23 is urged to a closed position by spring 23-2 supported by rib members 23-6. Valve 24 is urged to a closed position by spring 24-2.

Thus, fluid (blood) is prevented from passing between containers 10 and 17.

Figure 4:
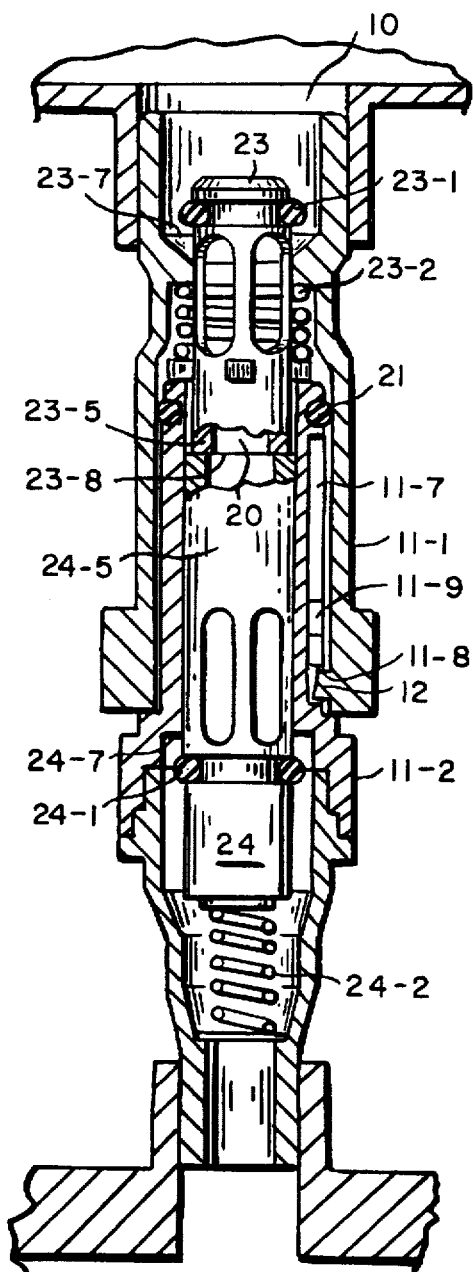
FIG. 4 is a sectional view of the valves and coupling positioned as shown in FIG. 2.

FIG. 4 shows the coupling device when the containers are moved to a second longitudinal position with the cam 12 positioned within groove 11-8. The valves 23 and 24 are opened as the movable sleeve 24-5 coupled to the valve 24 engages the sleeve member 23-5 of valve 23 at 23-8, which urges the O-ring 23-1 away from the valve seat 23-7 and at the same time due to resistance of the spring 23-2 causes the O-ring 24-1 away from valve seat 24-7. Thus, fluid can flow in passageway 20 between containers 10 and 17.

Figure 5:
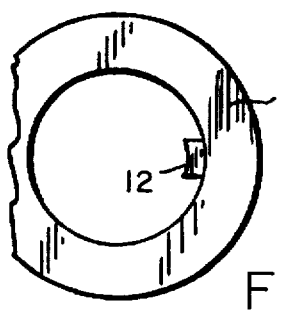
FIG. 5 is a sectional view of the valves and coupling in the position when the containers are separated.

FIG. 5 illustrates the female coupling member 11-1 and the male coupling member 11-2 separated, which is accomplished by tilting the male coupling member to separate cam 12 from longitudinal groove 11-7 to release the containers.

Figure 6:
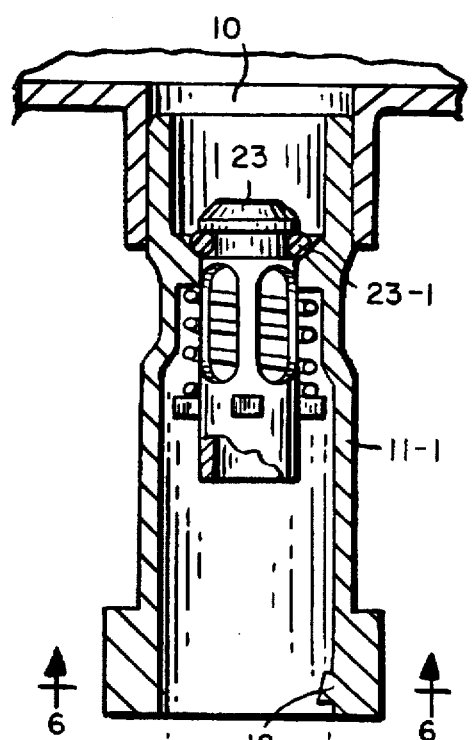
FIG. 6 shows an end view of the female coupling member along 6—6 of FIG. 5.

FIG. 6 shows an end view of the female coupling member illustrating cam 12.

Figure 7:
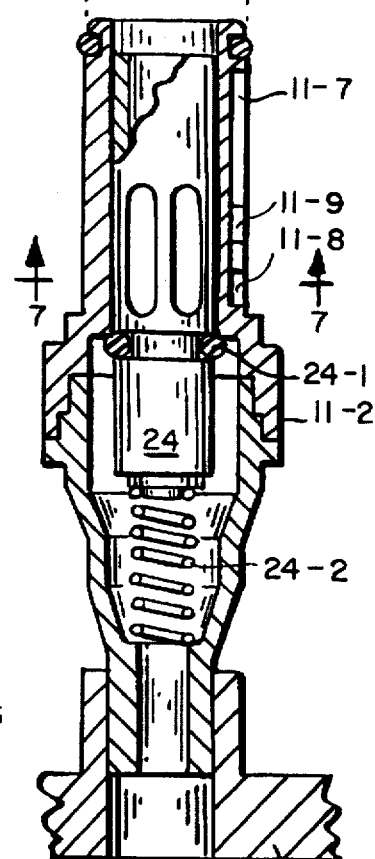
FIG. 7 shows an sectional view of the male coupling member along 7—7 of FIG. 5.

FIG. 7 shows a cross section of the male coupling member at longitudinal position groove 11-8. Preferably, the groove has a rounded bump 11-6 (or alternatively, e.g., a ramp or a wedge-shaped locking member), over which the cam 12 can be forced, but which provides a locked position, which takes a conscious force to overcome. This locking member 11-6 prevents casual disengagement of the coupling device. A similar locking member is also preferably positioned in groove 11-9. To facilitate assembly, another locking member can also be positioned to stop longitudinal movement in groove 11-7 at groove 11-9 and requiring conscious effort to move the coupling device closer together to open the valves by positioning the cam in groove 11-8.

Figures 8A, 8B, 8C:
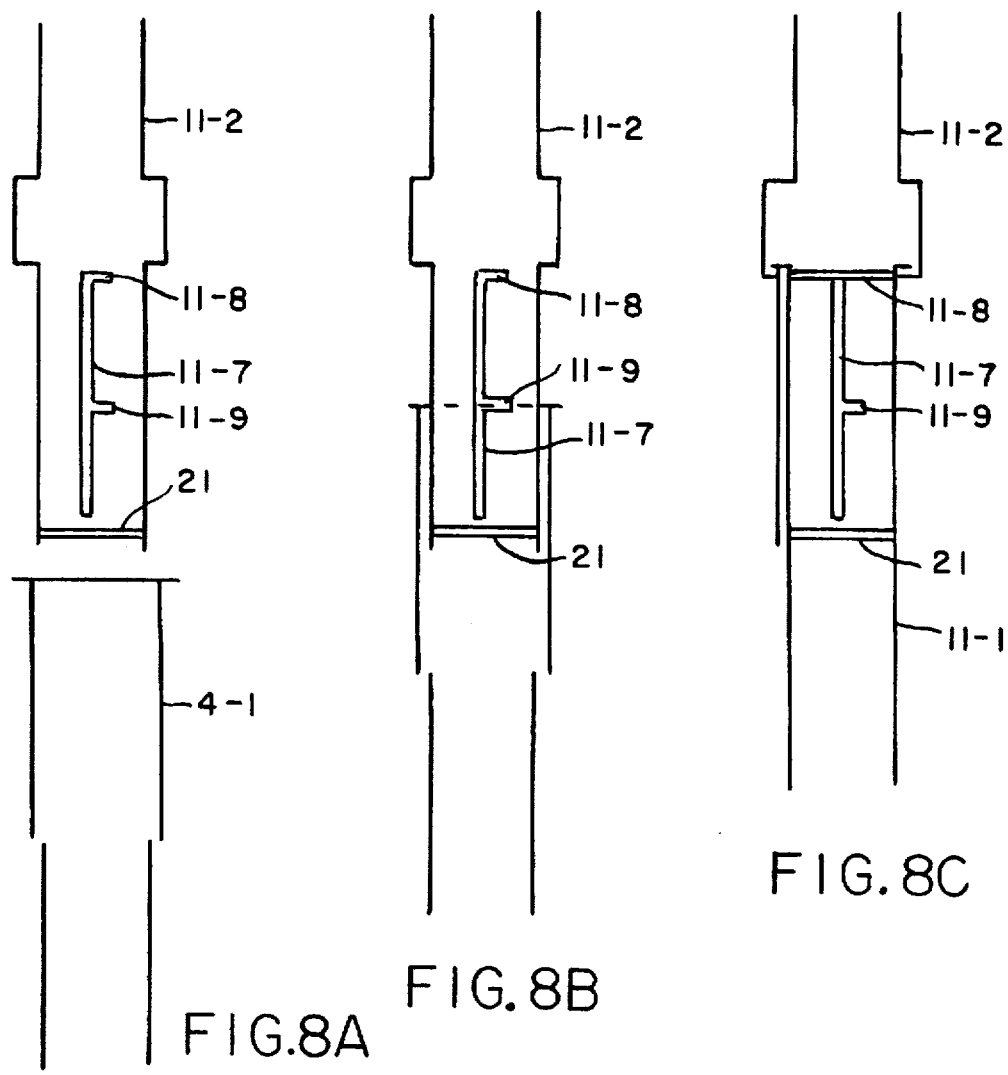
FIG. 8a is a schematic illustration of a coupling device of the present invention with the members separated showing one embodiment of a grooving pattern on the male coupling member.
FIG. 8b is a schematic illustration of a coupling device of the present invention with the members joined in the first longitudinal position.
FIG. 8c is a schematic illustration of a coupling device of the present invention with the members joined in the second longitudinal position.

FIGS. 8a–8c illustrate the grooves on the male coupling member and the two coupling members separated (FIG. 8a), joined in the first longitudinal position (FIG. 8b), and joined in the second longitudinal position (FIG. 8c). As illustrated in FIG. 8a, there is a longitudinal groove 11-7 in which cam 12 rides to move the coupling members closer together. First longitudinal position groove 11-9 is perpendicular and connected to groove 11-7. Second longitudinal groove 11-8 is also perpendicular and connected to groove 11-7. To assemble the coupling device, female coupling member 11-1 is tipped to insert cam 12 into groove 11-7 in the outer surface of male coupling member 11-2. The female coupling member is then slid longitudinally until cam 12 reaches lateral groove 11-9 and is rotated clockwise (as illustrated) until coming to a stop (illustrated in FIG. 7). In this position the coupling and attached containers are joined but the valves are closed. To open the valves, the female coupling member is rotated counterclockwise until cam 12 is stopped in groove 11-7, pushed forward until cam 12 reaches lateral groove 11-8, and rotated clockwise until coming to a stop (not shown). In this position, the valves are open and fluid can flow between the containers through passageway 20.

It should be understood because of the construction herein it is possible to connect the containers together in a sealed bag so that the user merely takes out the system and hangs it up for the future collection of blood since the containers are already coupled and sealed together as shown in FIG. 3. When the user e.g. nurse wants to collect blood, for reinfusion or for disposal, the coupling is locked into position shown in FIG. 4 for collection of blood. Preferably, when the two containers are hung vertically, the female coupling member is attached to the bottom container.

Figure 9:
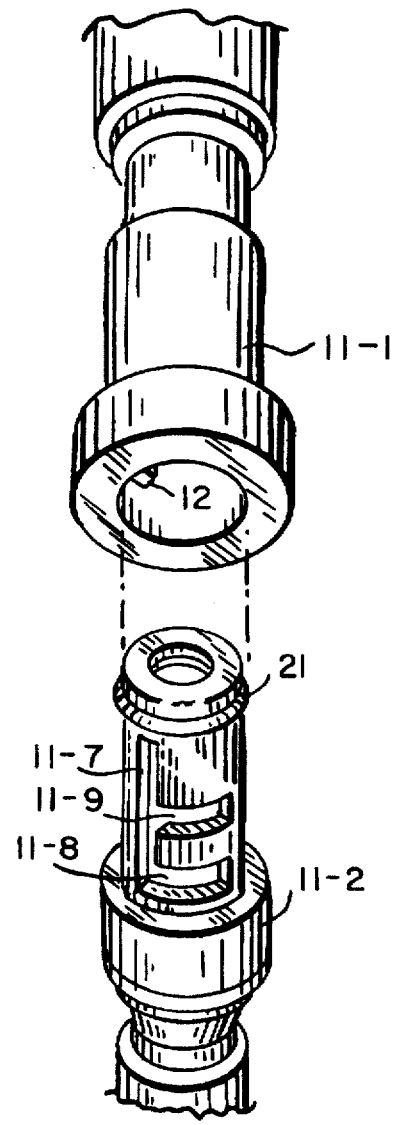
FIG. 9 shows, in perspective, a male and a female coupling member in accord with the present invention in a position to be joined to form a coupling.

FIG. 9 illustrates the relative positioning between the male coupling member and the female coupling member when they are being joined. The cam 12 of the female coupling member is positioned in the groove 11-7 of the male coupling member while the two members are held at an angle with respect to the longitudinal axes of the two members. After the cam 12 is engaged in the groove 11-7, the two members are straightened so that their longitudinal axes coincide, and the female coupling member is moved relative to the male coupling member guided by the cam 12 in groove 11-7 to the first longitudinal positioning groove 11-9, (extending perpendicularly circumferentially from groove 11-7), thereby holding the two members together with the valves closed. The cam 12 can later be moved to position it in the second longitudinal positioning groove 11-8 (also extending perpendicularly circumferentially from groove 11-7) to hold the members together with the valves open for passage of fluid through the coupling.

Figure 10:
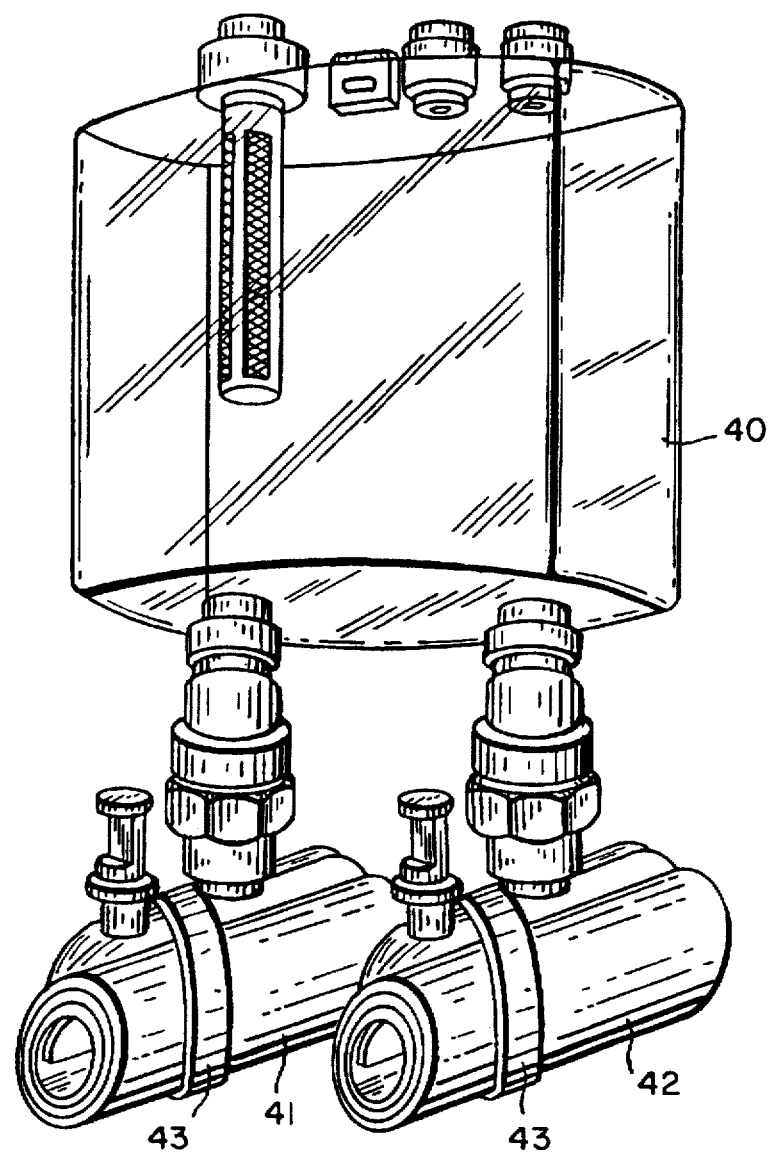
FIG. 10 shows, in perspective, a modified system for two containers to be filled from a single container.

In FIG. 10, there is shown a double bag system comprising first container 40 with rolled up bags (containers) 41 and 42, both bags 41 and 42 coupled through a coupling device as described herein and illustrated in FIGS. 3 to 8c. The plastic straps 43 holding the bags in a rolled positioned are removed e.g. unhooked or cut to let the bag 41 and 42 unroll and collect blood.

Figures 11A, 11B:
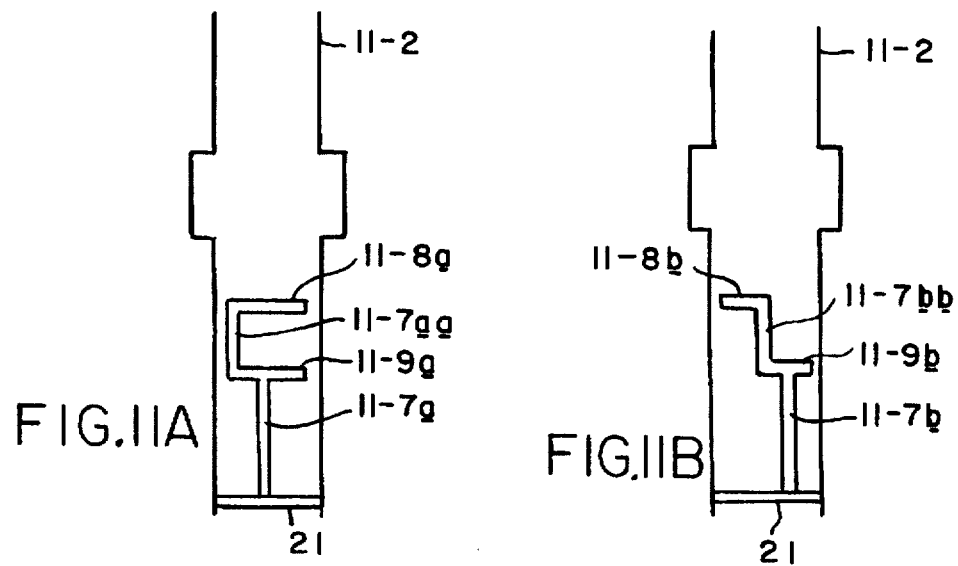
FIG. 11a and FIG. 11b are schematic illustrations showing alternative grooving patterns to that shown in FIGS. 8a–8c for a male coupling member.

FIGS. 11a and 11b illustrate alternative groove patterns for the male coupling member. In FIG. 11a, the longitudinal groove is shown in two sections 11-7a,11-7aa. This construction facilitates assembly of the coupling device because there is a stop when the cam reaches the first longitudinal position. In FIG. 11b, the longitudinal groove is also shown in two sections 11-7b,11-7bb and the second longitudinal position groove 11-8b extends in a direction opposite to the first longitudinal position groove 11-9b. Other groove patterns can also provide the benefits of the present invention.

The invention has been described in detail with reference to preferred embodiments thereof. However, it will be appreciated that, upon consideration of the present specification and drawings, those skilled in the art may make modifications and improvements within the spirit and scope of this invention as defined by the claims. For example, the groove pattern could be formed on the inside wall of the female coupling member and a cam to cooperate therewith could be located on the male coupling member. Also, other fluids, particularly biological fluids can be collected using the devices of the present invention.

I claim:

1. A blood collection system comprising a first container for collecting blood, a second container for receiving blood from said first container, a coupling device comprising first and second coupling members, each coupling member having a normally closed valve in a passageway connecting the members, the first coupling member having a groove pattern comprising a longitudinal groove and two grooves perpendicular to the longitudinal groove and connected therewith to provide longitudinal positioning stops for the two coupling members, the second coupling member having a cam, which can be positioned in the groove pattern and which cooperates with the groove pattern, said coupling device holding said first and second containers together in a first longitudinal position at a first longitudinal positioning stop with the valves thereof closed preventing flow of blood between the containers while preventing contamination of the blood passageway between the containers and, when the containers are moved relatively closer together to a second longitudinal position at a second longitudinal positioning stop, causing the opening of the valves in both coupling members to permit the flow of blood between the containers.

2. The system according to claim 1, wherein said coupling device includes a female coupling member and a male coupling member, the groove pattern being on the male coupling member and the cam on the female coupling member.

3. The system according to claim 2, wherein the groove pattern has a longitudinal groove in two sections, the first section ending at the first longitudinal positioning groove, and the second section connecting the first and the second longitudinal positioning grooves.

4. The system according to claim 1, wherein one or more protrusions are formed in the grooves to resist passage of the cam in the groove to prevent casual movement between the coupling members.

5. The system according to claim 1, wherein said coupling device includes a female coupling member and a male coupling member, the groove pattern being on the female coupling member and the cam on the male coupling member.

6. The system according to claim 5, wherein the groove pattern has a longitudinal groove in two sections, the first section ending at the first longitudinal positioning groove, and the second section connecting the first and the second longitudinal positioning grooves.

7. A coupling providing a contamination free liquid flow pathway between opposite ends thereof, said coupling comprising:

a female member having a passageway containing a valve assembly with a valve in a normally closed position; and a male member having a passageway containing a valve assembly with a valve in a normally closed position;

said male member having a groove pattern comprising a longitudinal groove and two grooves perpendicular to the longitudinal groove and connected therewith to provide longitudinal positioning stops for the two coupling members, the female member having a cam, which can be positioned in the groove pattern and which cooperates with the groove pattern, a first longitudinal positioning groove of the male member cooperating with the female member to join the male member and the female member together in a first longitudinal position wherein both valves remain closed to seal the passageway;

a second longitudinal positioning groove of the male member cooperating with the female member to join the male member and the female member together in a second longitudinal position wherein the opposing ends of the coupling are closer together and both valves are open and the passageway is open between opposing ends of the coupling.

8. The coupling of claim 7, wherein the groove pattern has a longitudinal groove in two sections, the first section ending at the first longitudinal positioning groove, and the second section connecting the first and the second longitudinal positioning grooves.

9. The coupling of claim 7, wherein one or more protrusions are formed in the grooves to resist passage of the cam in the groove to prevent casual movement between the coupling members.

10. A container for collecting samples, said container comprising an integrally connected female coupling member having a passageway containing a valve assembly with a valve in a normally closed position;

said female coupling member adapted to receive a male coupling member having a passageway containing a valve assembly with a valve in a normally closed position, wherein the female coupling member and the male coupling member provide a contamination free pathway between opposing ends of a coupling formed thereby;

the male member having a groove pattern comprising a longitudinal groove and two grooves perpendicular to the longitudinal groove and connected therewith to provide longitudinal positioning stops for the two coupling members, the female member having a cam, which can be positioned in the groove pattern and which cooperates with the groove pattern, a first longitudinal positioning groove of the male member cooperating with the female member to join the male member and the female member together in a first longitudinal position wherein both valves remain closed to seal the passageway;

a second longitudinal positioning groove of the male member cooperating with the female member to join the male member and the female member together in a second longitudinal position wherein the opposing ends of the coupling are closer together and both valves are open and the passageway is open between opposing ends of the coupling.

11. A container for collecting samples, said container comprising an integrally connected male coupling member having a passageway containing a valve assembly with a valve in a normally closed position;

said male coupling member adapted to be received in a female coupling member having a passageway containing a valve assembly with a valve in a normally closed position, wherein the female coupling member and the male coupling member provide a contamination free pathway between opposing ends of a coupling formed thereby;

the male member having a groove pattern comprising a longitudinal groove and two grooves perpendicular to the longitudinal groove and connected therewith to provide longitudinal positioning stops for the two coupling members, the female member having a cam, which can be positioned in the groove pattern and which cooperates with the groove pattern, first longitudinal positioning groove of the male member cooperating with the female member to join the male member and the female member together in a first longitudinal position wherein both valves remain closed to seal the passageway;

a second longitudinal positioning groove of the male member cooperating with the female member to join the male member and the female member together in a second longitudinal position wherein the opposing ends of the coupling are closer together and both valves are open and the passageway is open between opposing ends of the coupling.

* * * * *